(12) United States Patent
Smith et al.

(10) Patent No.: US 7,084,129 B1
(45) Date of Patent: *Aug. 1, 2006

(54) ANTIMICROBIAL QUATERNARY SURFACTANTS BASED UPON ALKYL POLYGLYCOSIDE

(75) Inventors: Dean A. Smith, Chattanooga, TN (US); David Anderson, Chattanooga, TN (US); Anthony J. O'Lenick, Jr., Dacula, GA (US)

(73) Assignee: Colonial Chemical, South Pittsburg, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/662,175

(22) Filed: Sep. 15, 2003

(51) Int. Cl.
*A01N 43/04* (2006.01)
*A61K 31/70* (2006.01)
*A61K 31/715* (2006.01)

(52) U.S. Cl. .......................... 514/53; 514/23
(58) Field of Classification Search ............. 514/23, 514/53
See application file for complete search history.

(56) References Cited

U.S. PATENT DOCUMENTS

| | | | |
|---|---|---|---|
| 3,087,230 A * | 4/1963 | Comire | 407/108 |
| 5,003,057 A | 3/1991 | McCurry | |
| 5,648,348 A | 7/1997 | Fost | |
| 6,846,846 B1 * | 1/2005 | Modak et al. | 514/722 |
| 7,008,930 B1 * | 3/2006 | O'Lenick et al. | 514/53 |
| 2003/0026833 A1 * | 2/2003 | Payne | 424/460 |
| 2004/0024068 A1 * | 2/2004 | Levy et al. | 514/575 |

* cited by examiner

*Primary Examiner*—Shaojia Anna Jiang
*Assistant Examiner*—Traviss McIntosh

(57) ABSTRACT

The invention relates to a series of polyglycoside derivatives that contain water-soluble cationic groups introduced into the molecule by reaction with the hydroxyl groups present in the starting polyglycoside molecule, with an epoxy cationic material. The materials are multifunctional, providing not only wetting, and conditioning, but also antimicrobial properties, making them ideal for personal care applications.

7 Claims, No Drawings

ANTIMICROBIAL QUATERNARY SURFACTANTS BASED UPON ALKYL POLYGLYCOSIDE

FIELD OF THE INVENTION

The present invention relates to the antimicrobial activity of a series of polyglycoside derivatives that contain water-soluble groups introduced into the molecule by reaction with the hydroxyl groups present in the molecule. These molecules are outstanding conditioners, are mild to the skin and eye, and are at the same time outstanding antimicrobial compounds in aqueous products. Cosmetic products made using these compounds not only are cosmetically elegant, but are are self preserving. Commercial alkyl polyglycosides generally have a low degree of polymerization of polysaccharide, in the molecule. This results in a molecule that is of limited water solubility. The present invention is aimed at functionalizing the hydrophobic alkyl polyglycoside, by including in the molecule phosphate, sulfate, sulfosuccinate, and carboxylate functionalities. These products have been called "alkyl glycosides, alkyl glycosides, alkyl polyglycosides or alkyl polyglycosides" by many different authors. All refer to the same molecules.

BACKGROUND

It is well known that there is a need for effective preservatives in a wide variety of applications where inhibiting the growth of microorganisms is necessary, as for example, personal care products such as shampoos, creams, lotions, cosmetics, liquid soaps, and household products such as fabric cleaners and softeners, hard surface cleaners and the like. The shelf life of these preparations depends on their resistance to microbial spoilage. In addition, antimicrobial agents are a matter of substantial commercial importance in many industrial applications and products such as in paint, wood, textiles, adhesives and sealants, leather, plastics, oil, rubber and metal working fluids etc.

Certain compounds have long been known and used commercially as preservatives. For example, 1,3-dimethylol-5,5-dimethylhydantoin (DMDMH) is useful as a formaldehyde donor for the preservation of personal care products, cosmetics and household products and halopropynyl carbamates are known for their fungicidal activity. Other commercially known preservatives include Quaternium-15 (DOWICIL 200 from Dow Chemical Company); Imidazolidinyl urea (GERMALL 115 from Sutton Laboratories); formaldehyde in the free state, as in formalin; alkyl parabens (e.g. methyl, ethyl and propyl) etc. While such materials have achieved commercial acceptance for many personal care and household products, they generally present a variety of limitations for such use including being unduly expensive; exhibiting limited anti-microbial or antifungal activity, or limited solubility in water; exhibiting undue pH dependence, adverse toxicological properties and skin sensitization or possible carcinogenicity; or they may be inactivated by commonly used materials.

Various synergistic combinations of ingredients have been also suggested for use as preservatives in certain applications such as, for example, disclosed in U.S. Pat. Nos. 3,699,231; 3,929,561; 4,454,146; 4,655,815; but these compositions generally exhibit unfavorable toxicity characteristics, particularly skin and eye irritation, and are not suitable for personal care and household products, and the development of effective, inexpensive, multifunctional products having a broad spectrum activity has long been sought.

U.S. Pat. No. 5,648,348 issued July 1997 to Fost et al discloses phospholipid based quats useful as antimicrobial. This patent, incorporated herein by reference, teaches that phospholipids can be employed as antimicrobials. These products contain phosphorus an element that has been implicated in blooms of algae in rivers and streams, making them very undesirable with today's environmentally concerned consumer.

It is highly desirable to have a product that is phosphate free for environmental reasons, is effective at controlling microbes and provides the cosmetic formulator with other formulation benefits in addition to preservation. One such example is if a molecule not only acts as a preservation system, but also provides conditioning in shampoos. The preservative in most cosmetic systems does nothing else but preserve the product from microbes, and is an expensive part of the formula. The compounds of the present invention provide conditioning, and outstanding wetting properties, are inherently non-toxic and non irritating.

None of the patents referenced above provide for such a multifunctional product. It was not until the present invention that all these desirable attributes were found in a single molecule.

THE INVENTION

It has been discovered that the particular series of quats derived from alkylpolyglycosides of the present invention are not only surprisingly and unexpectedly exhibit both broad spectrum bactericidal and fungicidal activity suitable for use as preservative and/or disinfectant agents in personal care and household products, but also are quite good conditioners and wetting agents.

Even very low concentrations of the compositions of the present invention exhibit effective antimicrobial activity and the antimicrobial compositions of the present invention are extremely well tolerated by human tissue, i.e., they exhibit exceptionally low ocular and skin irritation and oral toxicity. Moreover, they can be used in product formulations containing nonionic, anionic, amphoteric and/or cationic components without significant inhibition or reduction of the required antimicrobial activity. The antimicrobial agents of the invention may also be used in combination with other known antimicrobial agents, when desired for particular applications, to enhance the antimicrobial effectiveness thereof. In another aspect of the invention, there is provided a method of inhibiting the growth of microorganisms in personal care, household cleaning and the like products which comprises incorporating in a personal care or household cleaning formulation an antimicrobial effective amount of an antimicrobial compositions of the present invention. As used herein the phrases "antimicrobial" and "inhibiting microbial growth" describes the killing of, as well as the inhibition or control of the growth of bacteria (gram positive and gram negative), fungi, yeasts and molds.

The compositions of the present invention relate to the finding that the reaction of the rather hydrophobic alkyl polyglycosides with the proper reagent results in molecules that have improved water-solubility and consequently overcome many of the shortcomings of the alkyl polyglycosides itself. It is most interesting that the maximum amount of glycoside units per alkyl group that can be added using known technology is 1.5. This means that the product is a mixture of mono and di functional product. This product has the remaining fatty alcohol stripped off in an evaporative process. The resulting product is about 70% by weight of a product of a d.p. of 1, about 21% by weight of a product of a d.p. of 2, about 7% by weight of a product having a d.p. of 3, and about 2% by weight of a product that has a d.p. of 4.

We have surprisingly learned that taking the alkyl polyglycosides produced in the commercial process, with it's inherent lack of water solubility and reacting it to make cationic surface-active agents, results in a series of products that are much more usable in many applications. Simply put, alkyl polyglycosides make much better hydrophobic raw materials than finished surface-active agents. When some or all of the many hydroxyl groups are converted into cationic groups outstanding conditioning and water solubility results. The properties include not only conditioning, wetting and compatibility with anionic surfactants, but also include antimicrobial activity. This coupled with the fact that these molecules are phosphate free make them ideal "green products" for personal care applications.

SUMMARY OF THE INVENTION

The present invention is directed to novel antimicrobial agents, which surprisingly and unexpectedly exhibit excellent broad spectrum bactericidal and fungicidal activity and effectiveness and effectively inhibit the growth of a variety of bacteria, yeast and molds. Moreover, such active agents may be used in combination with or in the presence of anionic, nonionic, amphoteric and/or cationic surfactants without inhibition of the antimicrobial efficacy thereof and are virtually non-irritating to the skin and eyes; thus, such antimicrobial agents may be used in diverse formulations and applications.

As noted, the instant invention is based upon the discovery that the antimicrobial compounds of the invention described above are effective in controlling the growth of bacteria, yeasts and molds in diverse formulations and applications such as cosmetic toiletries, personal care, household and related products and materials. The antimicrobial agents of the invention are not only an effective antimicrobial for the destruction or control of fungi and bacteria that cause degradation and deterioration of diverse personal care and household product formulations, but also by their activity against the organisms that can reside and accumulate on various surfaces, can provide utility in sanitizing, disinfecting and bacteriostatic applications.

Alkyl polyglycosides are complex products made by the reaction of glucose and fatty alcohol. In dealing with the chemistry one talks about degree of polymerization (the so called "d.p."). In the case of traditional alkyl polyglycosides the d.p. is around 1.4. This means that on average thee is 1.4 units of glucose for each alkyl group. The fact of the matter is that the resulting material is a mixture having an average of 1.4.

The specific structure of the product is hard to ascertain completely since many positional isomers are possible, but two examples of structures are as follows:

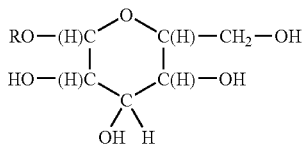

Alkyl polyglycosides (d.p. 1)

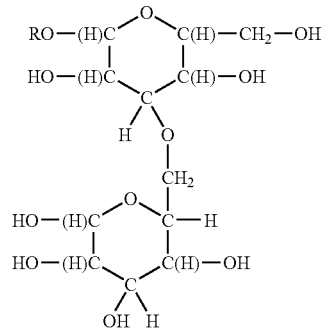

Alkyl polyglycosides (d.p. 2)

It should be clear that if there is a 50/50 mixture of the d.p. 1 and d.p. 2 product, the resulting analytical data will show that on average there is a d.p. of 1.5. Saying that a molecule has a d.p. of 1.5 does not mean that each molecule has 1.5 glucose units on it.

One key aspects of the present invention relates to the heretofore unappreciated fact that the rather hydrophobic alkyl polyglycosides contain on average five hydroxyl groups, one primary and the other four secondary. The assumption that there is a large degree of group specificity for the primary to react exclusively rather than the four additional hydroxyl groups is simply not true. This means that if on average only one of the five groups is reacted, there remains a very large concentration of reacting alkyl polyglycoside that has no functionality on it. Since the reactant with no functionalization remain water insoluble, there needs to be at lease 2 and as many as 4 hydroxyl groups functionalized to get to the desired water-soluble product. We have observed that when between 2 and 5 groups are reacted, a water-soluble very useful product results. Therefore it is a preferred embodiment having between 2 and 5 of the hydroxyl groups functionalized.

Another key unappreciated fact in making the compounds of the present invention is the selection of the proper reagents to make the desired product. Specifically, the reaction of the alkyl polyglycoside with a certain family of epoxy compounds and related materials occurs under mild aqueous conditions and results in a mild cationic conditioner useful in hair and skin care products.

DETAILED DESCRIPTION OF THE INVENTION

The compositions of the present invention are mixtures conform to the following structures:

(a)

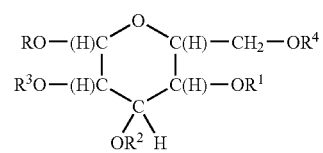

wherein;

R is alkyl having 8 to 22 carbon atoms;

$R^1$, $R^2$, $R^3$ and $R^4$ are independently selected from the group consisting of

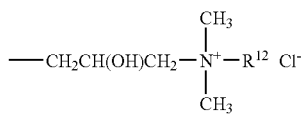

and H, with the proviso that $R^1$, $R^2$, $R^3$. and $R^4$ are not all H;

$R^{12}$ is $CH_3(CH_2)_n-$ n is an integer ranging from 0 to 21.

and (b)

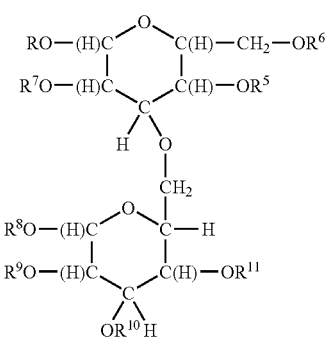

wherein;

R is alkyl having 8 to 22 carbon atoms;

$R^1$, $R^2$, $R^3$ and $R^4$, $R^5$, $R^6$, $R^7$, $R^8$, $R^9$, $R^{10}$, and $R^{11}$ are independently selected from the group consisting of

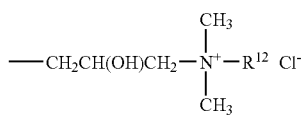

and H, with the proviso that $R^1$, $R^2$, $R^3$. and $R^4$ are not all H;

$R^{12}$ is $CH_3(CH_2)_n-$ n is an integer ranging from 0 to 21.

Another aspect of the present invention is a process for conditioning hair and skin which comprises contacting the hair and skin with an effective conditioning concentration of a composition conforming to the following:

(a)

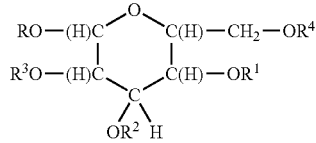

wherein;

R is alkyl having 8 to 22 carbon atoms;

$R^1$, $R^2$, $R^3$ and $R^4$ are independently selected from the group consisting of

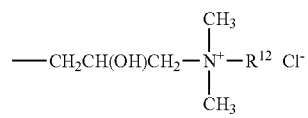

and H, with the proviso that $R^1$, $R^2$, $R^3$. and $R^4$ are not all H;

$R^{12}$ is $CH_3(CH_2)_n-$ n is an integer ranging from 0 to 21;

and (b)

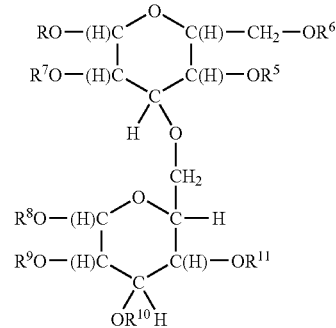

wherein;

R is alkyl having 8 to 22 carbon atoms;

$R^1$, $R^2$, $R^3$ and $R^4$, $R^5$, $R^6$, $R^7$, $R^8$, $R^9$, $R^{10}$, and $R^{11}$ are independently selected from the group consisting of

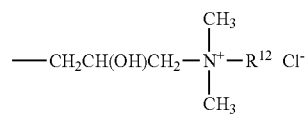

and H, with the proviso that $R^1$, $R^2$, $R^3$. and $R^4$ are not all H;

$R^{12}$ is $CH_3(CH_2)_n-$ n is an integer ranging from 0 to 21.

Preferred Embodiment

In a preferred embodiment n is 0.
In a preferred embodiment n is 11.
In a preferred embodiment n is 13.
In a preferred embodiment n is 17.
In a preferred embodiment n is 19.
In a preferred embodiment n is 21.

EXAMPLES

Preparation of Alkyl Glycosides

Alkyl Glycosides are raw materials used to make the surface-active polyglycoside derivatives of the present invention.

Saccharides useful in the process of making alkyl glycosides are saccharides that can be alkylated in the "1" position, commonly referred to as "reducing saccharides", or higher saccharides that can be hydrolyzed to provide such a saccharide. These saccharides are typically comprised of aldo- or keto-hexoses or pentoses.

Examples of saccharides include glucose (dextrose), fructose, mannose, galactose, talose, allose, altrose, idose, arabinose, xylose, lyxose, and ribose. Examples of hydrolyzable saccharides that are a source of reducing saccharides include starch, maltose, sucrose, lactose, maltotriose, xylobiose, mellibiose, cellobiose, raffinose, stachiose, methyl glycosides, butyl glycosides, levoglucosan, and 1,6-anhydroglucofuranose.

The physical form of the saccharide may vary. The saccharide will typically be in a fluid (as opposed to a solid) state, e.g. as a melt or an aqueous syrup, during at least a portion of the period of reaction, if not for a predominant portion of the period of the reaction. Crystalline (e.g. anhydrous or hydrates) or amorphous saccharide solids in various particle sizes, e.g. granules, powders, etc., can be used, but the heating of the reaction medium may well fluidize at least a portion of a solid reactant, if not a predominant portion of the saccharide reactant. Aqueous syrups of saccharides, typically at saccharide solids of between about 10% and 90% dry solids by weight can also be used. Indeed, the use of the hydrophobic catalysts of this invention should show the most improved results over conventional catalysts in the context of the use of aqueous syrup reactants as compared with processes which employ solid saccharide reactants, particularly with respect to avoiding the formation of deleterious amounts of polysaccharides and very high DP alkyl glycosides during the glycoside formation reaction.

The preferred saccharides are glucose, galactose, xylose and arabinose, or mixtures thereof, for reasons of availability, low cost, and convenience. Glucose in the anhydrous crystalline form is preferred, although dextrose monohydrate, corn syrups of high dry solids (typically 50% to 80% dry solids) and a high dextrose equivalence (D.E.) (typically greater than 90 D.E and most commonly 95 D.E.) can be commonly employed. Indeed, while the higher the purity of the dextrose source, the better the quality of the product (other things being equal), the catalysts of this invention allow the use of a lower purity dextrose source and yet yield a product of substantially equivalent quality as compared with prior catalysts. Because of the ready availability of glucose and its oligomers, much of the remaining description is particularly suited to the use of glucose in its various forms.

Alcohols useful in the process of this invention are hydroxyl-functional organic compounds capable of alkylating a saccharide in the "1" position. The alcohol can be naturally occurring, synthetic, or derived from natural sources and/or derivatized. Examples include monohydric alcohols (more fully discussed below) and polyhydric alcohols (e.g. ethylene glycol, propylene glycol, polyethylene glycols, polypropylene glycols, butylene glycol, glycerol, trimethylolpropane, pentaerythritol, polyester polyols, polyisocyanate polyols, and so on). Other examples include aromatic alcohols such as benzyl alcohol, phenol, substituted phenols (e.g. alkylphenols) and alkoxylates of each.

Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. In general, these alcohols have minimal solvent power for the saccharide molecule. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, pentacosyl alcohol, oleyl alcohol, linoleyl alcohol, isoborneol alcohol, hydroabietyl alcohol, phenoxyethanol, phenoxypolyethoxyethanol containing five ethoxy groups, 2-methyl-7-ethyl-4-undecanol, and mixtures of one or more of the above.

A preferred group of alcohols are alkanols having the formula ROH wherein R represents an alkyl group having from 8 to 30 carbon atoms. A particularly preferred group of alcohols are those wherein R represents an alkyl radical having from 8 to 20, preferably 11 to 18, carbon atoms. The alkyls can be straight or branched chain.

Alkyl Glycoside Examples

Example 1

A one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 602.4 g (3.105 moles) of a commercial mixture of $C_{11}$ to $C_{15}$ (98% $C_{12}$ and $C_{13}$) straight and branched alkanols (Neodol 23 available form Shell Chemical Co.) and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.™. wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4.

Example 2–8

The same one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 3.105 moles of the specified alcohol and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in H$_2$O) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact.™. wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4. The hydroxyl value was run on the resultant product and is indicated below.

| Example | Alkyl | OH Value |
| --- | --- | --- |
| 2 | C12H25 | 691.9 |
| 3 | C10H21 | 741.8 |
| 4 | C8H17 | 795.4 |
| 5 | C14H27 | 653.8 |
| 6 | C18H37 | 584.4 |
| 7 | C18H35 | 586.7 |
| 8 | C20H42 | 555.1 |

Alkyl Polyglycoside Quaternary Compounds

There are a number of water-soluble groups that can be introduced into the finished alkyl polyglycoside. These include phosphates; sulfates, sulfosuccinate, and carboxylate groups.

It will be clearly understood that the alkyl polyglycosides of the present invention have a number of hydroxyl groups present in the molecule. The number of hydroxyl groups functionalized will have a profound effect upon the degree of increased water solubility of the molecule.

The present invention includes a functionalization of a low number of hydroxyl groups (one per molecule) to a high number (all groups on the molecule). The preferred number to functionalize is an intermediate number of groups (approximately half of the number present).

One of the reactants of the present invention is the alkyl polyglycoside, the other a specific type of compounds conforming to the following structure;

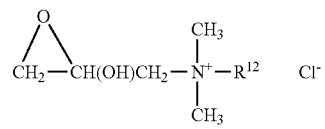

$R^{12}$ is $CH_3(CH_2)_n$—

The reaction sequence is as follows:

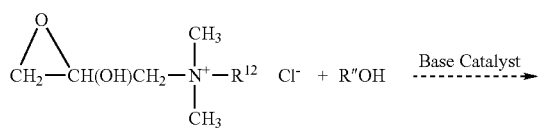

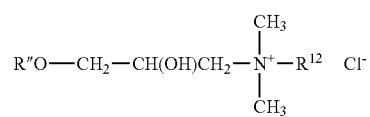

Epoxy Reactants

The reactants useful in the synthesis of the products of the current invention are commercially available and come from DeGussa and others.

| Example | n Value |
| --- | --- |
| 9 | 0 |
| 10 | 11 |
| 11 | 13 |
| 12 | 17 |
| 13 | 19 |
| 14 | 21 |

General Procedure—To a flask equipped with agitation, heat, thermometer and nitrogen sparge is added the specified amount of the specified alkyl polyglycoside and enough water to make the final product have a solids of 35% by weight. The alkyl polyglycoside is heated to melt. Next, the specified amount of epoxy reactant (examples 9–14) is added under good agitation and nitrogen sparge. Next is added 0.5% sodium methylate. The % is by weight and is based upon the total amount of all materials reacted. Nitrogen sparge is simply nitrogen bubbled through the liquid contents of the flask. This keeps the color light, minimizing oxidation and color formation. The reaction mass is heated to 90–100° C., and is held for 5–8 hours. Testing for loss of the epoxy group follows the reaction progress. Once the theoretical value is reached, the reaction is terminated and the product is used without additional purification.

It will be clearly understood that the alkyl polyglycoside has on average five hydroxyl groups when the d.p. is 1.4. The phosphation can include all five, but in a more preferred embodiment includes between one and three hydroxyl groups. This ratio provides the best degree of water solubility. The most preferred number of hydroxyl groups to phosphate is 2.

Example 15–16

| | Alkyl polyglycoside | | Epoxy Reactant | | Water | OH Groups |
|---|---|---|---|---|---|---|
| Example | Example | Grams | Example | Grams | Grams | Reacted |
| 15 | 1 | 446.0 | 9 | 765.0 | 2249.0 | 5 |
| 16 | 2 | 416.0 | 10 | 614.0 | 1912.0 | 2 |
| 17 | 3 | 388.0 | 11 | 1005.0 | 2587.0 | 3 |
| 18 | 4 | 472.0 | 12 | 1173.0 | 3055.0 | 3 |
| 19 | 5 | 528.0 | 13 | 840.0 | 2540.0 | 2 |
| 20 | 6 | 526.0 | 14 | 894.0 | 2637.0 | 2 |
| 21 | 6 | 526.0 | 9 | 306.0 | 1396.0 | 2 |
| 22 | 5 | 528.0 | 10 | 163.0 | 1075.0 | 1 |
| 23 | 4 | 472.0 | 11 | 914.0 | 2275.0 | 2 |
| 24 | 3 | 388.0 | 12 | 782.0 | 2328.3 | 2 |
| 25 | 2 | 416.0 | 13 | 419.0 | 2012.0 | 1 |
| 26 | 1 | 446.0 | 14 | 447.0 | 1807.0 | 1 |

The compounds of the invention range from clear yellow liquids to pastes. Generally is the n value is over 13, a paste results. The compounds are compatible with anionic surfactants like lauryl ether sulfates and are highly conditioning to the hair, providing soft smooth hair.

The antimicrobial activity of the compounds described above has been confirmed using standard laboratory techniques, including the Minimum Inhibitory Concentration (MIC) technique. They have been found effective, for example, in inhibiting bacteria including *S. aureus, E. coli, P. aeruginosa* and *S. choleraesuis*. They have also been found effective against yeast and mold including *C. albicans* and *A. niger*. In these tests it has been determined that the presence of anionic, nonionic, amphoteric and/or cationic materials did not inhibit the antimicrobial efficacy nor did a variety of inactivators commonly encountered in personal care and household applications. The broad spectrum preservative characteristics of the antimicrobial phospholipids of the invention in typical cosmetic formulations have also been established and confirmed.

Specifically, molds and yeasts which may be inhibited include *Aspergillus niger, Candida albicans* plus various species of *Penicillium, Tricholphyton, Alternaria, Gliocladium, Paecilomyces, Mucor, Fusarium, Geotrichum, Cladosporium* and *Trichoderma*. Examples of the bacteria include *Salmonella choleraesuis, Serratia marcescens, Klebsiella pneumoniae, Enterobacter aerogenes, Aerobacter aerogenes, Proteus vulgaris, Streptococcus faecalis, Pseudomonas aeruginosa, Escherichia coli, Staphylococcus aureus, Staphylococcus epidermidis, M. luteus, P. mirabilis, P. cepacia, P. stutzeri* and *A. hydrophilia*.

Another aspect of the present invention is the discovery that the antimicrobial phospholipid compounds surprisingly and unexpectedly exhibit significant spermicidal and antiviral activity which further enhances the utility of the compounds of the invention for a diversity of applications.

The antimicrobial compounds described above have activity against bacteria, yeasts and molds when employed at appropriate levels of concentration and may be used to inhibit growth or effectively destroy these organisms. It should be obvious that the required effective concentration or amount will vary with particular organisms and also on a number of other factors in particular applications. In general, however, effective antimicrobial response is obtained when the active agent is employed in concentrations ranging between 5 and 10,000 ppm (parts per million) and preferably between about 50 and 1,000 ppm. Generally, the concentration of the agent required for bactericidal activity will be lower than the concentration required for fungicidal activity.

A study was conducted by Bio-Control Consultants Inc. 43 Mohican Drive Westfield N.J. 07090. The purpose was to determine the antimicrobial capability of the compounds of the present invention (alkylpolyglucoside quats) utilizing the zone inhibition technique. The test materials were evaluated for gross antimicrobial activity against a series of four (4) test organisms: *Pseudomonas aeruginosa* (Gram negative bacteria); *Staphylococcus aureus* (Grain positive bacteria); *Candida albicans* (yeast) and *Aspergillus niger* (mold) utilizing the zone inhibition technique. Results of the assays are presented below.

Agar was prepared and inoculated with the test organism, then poured into a plate. The examples chosen were diluted to 0.1, 0.2 and 0.4 and applied to a cellulose disc, and allowed to dry. The dry cellulose disc was applied to the hard agar and the agar was placed in an incubator to allow the organisms to grow.

| SCORING: | 1 = Excellent; |
|---|---|
| | 2 = Very Good; |
| | 3 = Good; |
| | 4 = OK (moderate); |
| | 6 = Poor; |
| | 8 = No Activity |

Applications Results

| SAMPLE | Sa | Psa | Ca | An | Score | Comments |
|---|---|---|---|---|---|---|
| Example 18 | 2 | 8 | 3 | 6 | 19 | Good on gram negative, gram positive, yeast and mold |
| Example 23 | 1 | 2 | 3 | 8 | 14 | Good on Bacterial and Yeast No Mold Activity |
| Example 22 | 1 | 2 | 1 | 2 | 6 | Excellent Activity overall |

The lower the score, the greater the activity.

Results

The analysis was run it triplicate and the average reported. The salient test is clarity, it indicates an ability to inhibit microbial growth. The "mm value" indicates the millimeters that the compound spread out from the disc.

| SAMPLE/% | Sa mm | Sa clarity | Psa mm | Psa clarity | Ca mm | Ca clarity | An mm | An clarity | Average Score |
|---|---|---|---|---|---|---|---|---|---|
| Applications Example 18 | | | | | | | | | |
| 0.4% | 11 | 4+ | 0 | 0 | 8 | 3+ | 8 | 1+ | |
| 0.2% | 9 | 3+ | 0 | 0 | 8 | 3+ | 0 | 0 | 19 |
| 0.1% | 8 | 3+ | 0 | 0 | 8 | 2+ | 0 | 0 | |
| Applications Example 23 | | | | | | | | | |
| 0.4% | 13 | 4+ | 10 | 4+ | 9 | 3+ | 0 | 0 | |
| 0.2% | 12 | 4+ | 8 | 3+ | 8 | 1+ | 0 | 0 | 14 |
| 0.1% | 10 | 4+ | 8 | 3+ | 8 | 0 | 0 | 0 | |
| Applications Example 22 | | | | | | | | | |
| 0.4% | 12 | 4+ | 10 | 4+ | 9 | 4+ | 9 | 4+ | |
| 0.2% | 12 | 4+ | 8 | 3+ | 9 | 4+ | 8 | 3+ | 6 |
| 0.1% | 12 | 4+ | 8 | 3+ | 9 | 4+ | 08 | 3+ | |

NOTES:
4+ = Excellent Activity;
0 = No Activity;
mm = Zone Size.

The product of Example 18 demonstrated antimicrobial activity.

Applications Example 2 displayed very good activity against the bacteria and acceptable activity against the yeast. There was, however, no apparent activity against the mold, *Aspergillus niger*

Applications Example 3 showed good activity against *Staphlococcus areus* and *Candida Albacans*.

The compounds of the present invention are outstanding antimicrobials, are mild to the eye and skin and offer outstanding conditioning effects on hair and skin and are good wetting agents. This makes them good candidates for self preserving cosmetic products. In addition they can be employed at concentrations of as low as 1% in towellettes applications also called baby wipes, where they provide gentle cleansing, resist microbial contamination and keep all the non woven towel in the container wet out and ready to use. Less efficient wetting agents result in dry towels on the top of the package, causing the consumer to need to turn the package over before use.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A method for inhibiting microbial growth which comprises contacting a substrate with an antimicrobially effective amount of a composition comprising a mixture conforming to the following structures:

(a)
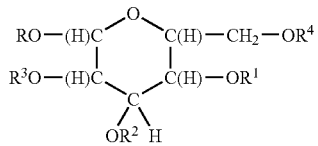

wherein;
R is alkyl having 8 to 22 carbon atoms;
$R^1$, $R^2$, $R^3$ and $R^4$ are independently selected from the group consisting of

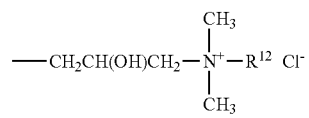

and H, with the proviso that $R^1$, $R^2$, $R^3$, and $R^4$ are not all H;
$R^{12}$ is $CH_3(CH_2)_n-$
n is an integer ranging from 0 to 21;
and
(b)

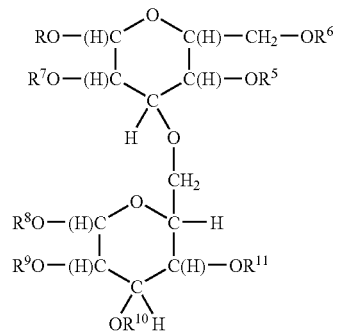

wherein;

R is alkyl having 8 to 22 carbon atoms;

$R^1$, $R^2$, $R^3$ and $R^4$, $R^5$, $R^6$, $R^7$, $R^8$, $R^9$, $R^{10}$, and $R^{11}$ are independently selected from the group consisting of

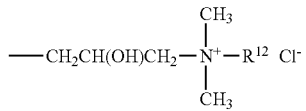

and H, with the proviso that $R^1$, $R^2$, $R^3$, and $R^4$ are not all H;

$R^{12}$ is $CH_3(CH_2)_n$— n is an integer ranging from 0 to 21.

2. A method of claim 1 wherein n is 0.

3. A method of claim 1 wherein n is 11.

4. A method of claim 1 wherein n is 13.

5. A method of claim 1 wherein n is 17.

6. A method of claim 1 wherein n is 19.

7. A method of claim 1 wherein n is 21.

\* \* \* \* \*